United States Patent

(12) United States Patent
Wang

(10) Patent No.: US 11,535,605 B2
(45) Date of Patent: Dec. 27, 2022

(54) ELECTROLUMINESECENT MATERIAL, METHOD FOR MANUFACTURING THE SAME AND A LUMINESECENT DEVICE WITH THE ELECTROLUMINESECENT MATERIAL

(71) Applicant: Wuhan China Star Optoelectronics Semiconductor Display Technology Co., Ltd., Wuhan (CN)

(72) Inventor: Yanjie Wang, Wuhan (CN)

(73) Assignee: Wuhan China Star Optoelectronics Semiconductor Display Technology Co., Ltd., Wuhan (CN)

(*) Notice: Subject to any disclaimer, the term of this patent is extended or adjusted under 35 U.S.C. 154(b) by 0 days.

(21) Appl. No.: 16/641,853

(22) PCT Filed: Dec. 30, 2019

(86) PCT No.: PCT/CN2019/129725
§ 371 (c)(1),
(2) Date: Feb. 25, 2020

(87) PCT Pub. No.: WO2021/036140
PCT Pub. Date: Mar. 4, 2021

(65) Prior Publication Data
US 2022/0274953 A1 Sep. 1, 2022

(30) Foreign Application Priority Data
Aug. 28, 2019 (CN) .......................... 201910800149.0

(51) Int. Cl.
*H01L 51/00* (2006.01)
*C07D 401/12* (2006.01)
(Continued)

(52) U.S. Cl.
CPC ............ *C07D 401/12* (2013.01); *C09K 11/06* (2013.01); *H01L 51/0072* (2013.01);
(Continued)

(58) Field of Classification Search
CPC .......................... H01L 51/0072; C07D 401/12
See application file for complete search history.

(56) References Cited

U.S. PATENT DOCUMENTS 7,154,114 B2 * 12/2006 Brooks ................... H05B 33/14
257/40
9,685,617 B2 * 6/2017 Beers ................... H01L 51/0085
(Continued)

FOREIGN PATENT DOCUMENTS

| CN | 105669977 A | 6/2016 |
| CN | 106589324 A | 4/2017 |

(Continued)

OTHER PUBLICATIONS

Organic Chemistry vol. 1.

*Primary Examiner* — Douglas M Menz
(74) *Attorney, Agent, or Firm* — PV IP PC; Wei Te Chung; Ude Lu

(57) ABSTRACT

The present disclosure provides an electroluminescent material, a method for manufacturing the electroluminescent material, and a luminescent device, by employing different electron donor units and electron acceptor units of acridine and carbazoles, and using two different donors to connect to an acceptor to form an asymmetric structure, an electroluminescent material, a method for manufacturing the electroluminescent material, and a luminescent device capable of emitting dark blue light with a high luminous efficiency are achieved.

17 Claims, 3 Drawing Sheets

(51) Int. Cl.
*C09K 11/06* (2006.01)
*H01L 51/50* (2006.01)
(52) U.S. Cl.
CPC ...... *H01L 51/0007* (2013.01); *H01L 51/5012* (2013.01); *H01L 2251/552* (2013.01)

(56) References Cited

U.S. PATENT DOCUMENTS

| | | | | |
|---|---|---|---|---|
| 11,322,690 | B2* | 5/2022 | Falber | C07D 519/00 |
| 2014/0249606 | A1* | 9/2014 | Pan | H01L 51/5032 |
| | | | | 585/27 |
| 2016/0072082 | A1* | 3/2016 | Brooks | H01L 27/32 |
| | | | | 546/4 |
| 2018/0130955 | A1* | 5/2018 | Pan | H01L 51/0071 |
| 2019/0207128 | A1* | 7/2019 | Brooks | H01L 51/0087 |
| 2019/0296242 | A1* | 9/2019 | Burkhart | H01L 51/0043 |

FOREIGN PATENT DOCUMENTS

| | | |
|---|---|---|
| CN | 108658940 A | 10/2018 |
| CN | 110563646 A | 12/2019 |
| CN | 110577513 A | 12/2019 |
| KR | 20170131730 A | 11/2017 |
| WO | 2016017741 A1 | 2/2016 |

\* cited by examiner

ELECTROLUMINESECENT MATERIAL, METHOD FOR MANUFACTURING THE SAME AND A LUMINESECENT DEVICE WITH THE ELECTROLUMINESECENT MATERIAL

BACKGROUND OF INVENTION

Field of Invention

The present application relates to a display field, and particularly to an electroluminescent material, a method for manufacturing the electroluminescent material, and a luminescent device.

Description of Prior Art

In prior art, the organic light emitting diodes have self-luminous characteristics, and electroluminescent material is a material that mainly dominates emitted light. However, luminous efficiency of the present electroluminescent material capable of emitting blue light is low, therefore, it is necessary to provide an electroluminescent material, a method for manufacturing the electroluminescent material, and a luminescent device capable of emitting dark blue light with a high luminous efficiency.

SUMMARY OF INVENTION

The present disclosure provides an electroluminescent material, a method for manufacturing the electroluminescent material, and a luminescent device to achieve an electroluminescent material and a device with a high luminous efficiency.

The present disclosure provides an electroluminescent material, wherein a structural formula of the electroluminescent material is $R_3$—$R_1$—$R_2$, wherein a structural formula of the $R_1$ group is selected from one of

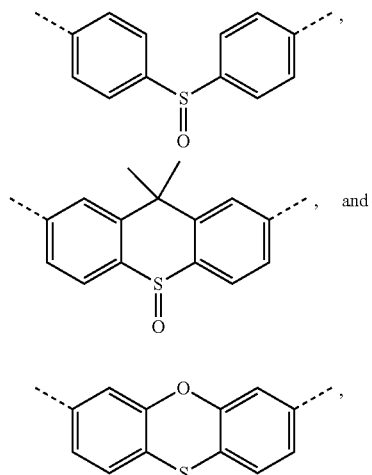

a structural formula of the $R_2$ group is selected from one of

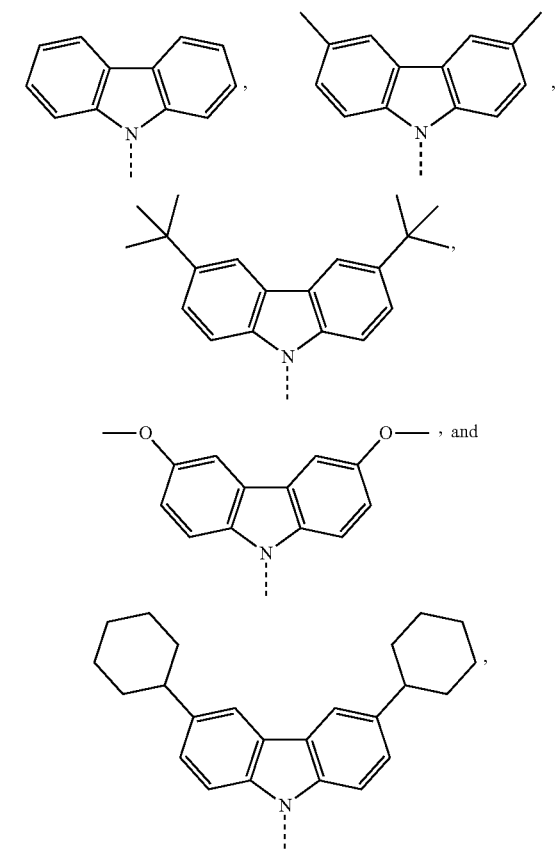

a structural formula of the $R_3$ group is selected from one of

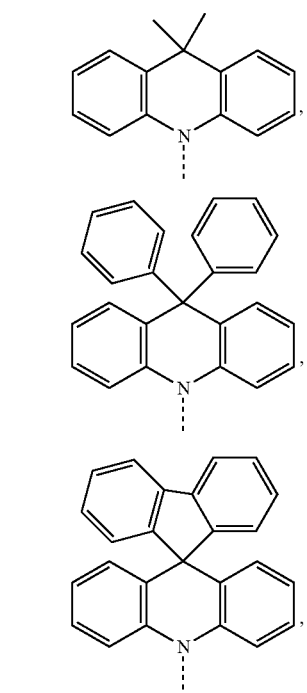

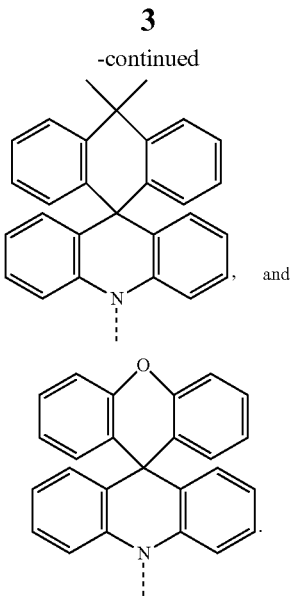

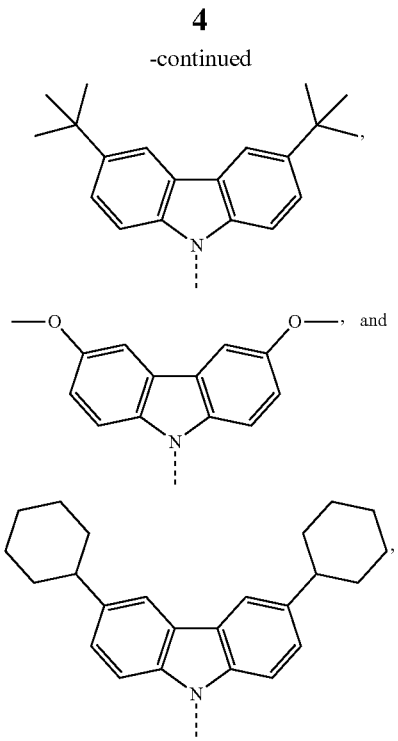

In the electroluminescent material, a peak value of a fluorescence emission of the electroluminescent material is between 425 nm and 450 nm.

The present disclosure provides a method for manufacturing an electroluminescent material, comprising:

providing a first reactant and a second reactant, and reacting the first reactant and the second reactant to generate a first intermediate product, wherein a structural formula of the first reactant is $X_1$—$R_4$—$X_2$, wherein a structural formula of the $R_4$ group is selected from one of

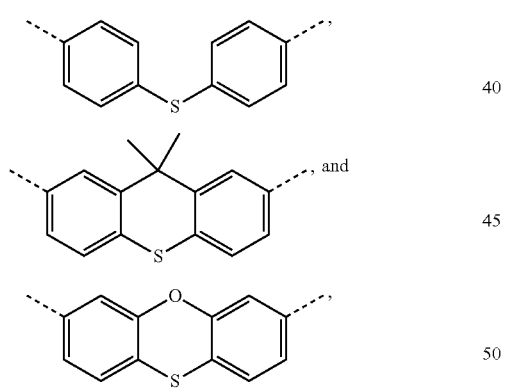

$X_1$ group is Cl or Br, the $X_2$ group is Br or I, the $X_1$ group is different from the $X_2$ group, the second reactant comprises a compound containing a $R_2$ group, a structural formula of the $R_2$ group is selected from one of

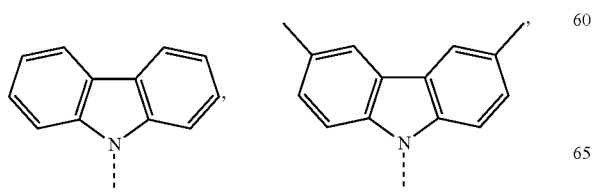

a structural formula of the first intermediate product is $X_1$—$R_4$—$R_2$;

providing a third reactant, and reacting the third reactant and the first intermediate product to generate a second intermediate product, wherein the third reactant comprises a compound containing a $R_3$ group, a structural formula of the $R_3$ group is selected from one of

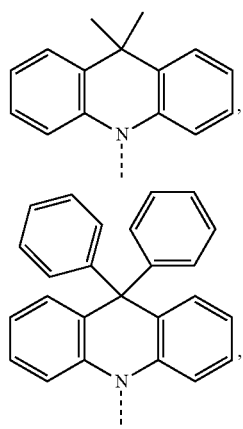

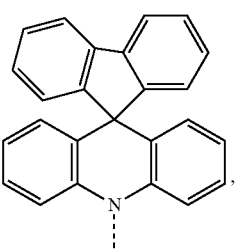

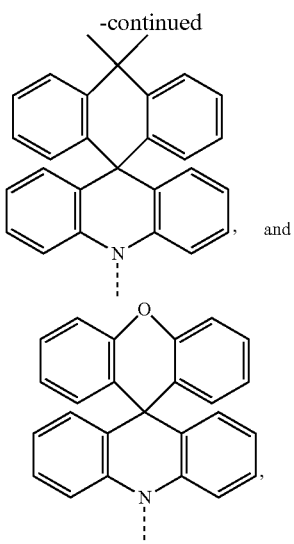

, and a structural formula of the second intermediate product is $R_3—R_4—R_2$; and providing a fourth reactant, and reacting the second intermediate product and the fourth reactant to generate the electroluminescent material, wherein the fourth reactant is an oxidizing agent, a structural formula of the electroluminescent material is $R_3—R_1—R_2$, a structural formula of the $R_1$ group is selected from one of

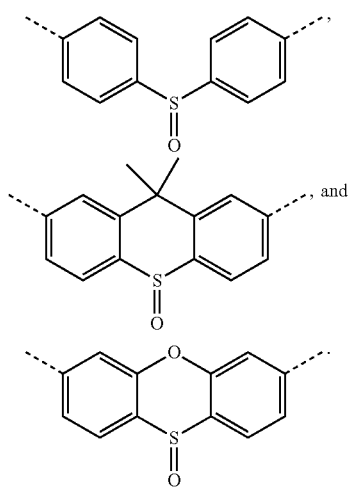

In the method for manufacturing the electroluminescent material, in the step of reacting the first reactant and the second reactant to generate a first intermediate product, a relationship between a molar weight of the first reactant and a molar weight of the second reactant is that for 10 millimoles of the first reactant, there are 5 millimoles-15 millimoles of the second reactant.

In the method for manufacturing the electroluminescent material, the first reactant and the second reactant are reacted in a first solvent to generate the first intermediate product, the first solvent comprises one or a group selected from N, N-dimethylformamide, dimethylacetamide, toluene, aniline, ethylbenzene, mesitylene, benzaldehyde, diphenyl ether, xylene, diethylbenzene, and chlorobenzene.

In the method for manufacturing the electroluminescent material, the first solvent comprises a first additive, the first additive comprises one or a group selected from CuI, Cu, potassium carbonate, tri-tert-butylphosphine tetrafluoroborate, sodium tert-butoxide, potassium hydroxide, sodium hydroxide, sodium carbonate and sodium bicarbonate.

In the method for manufacturing the electroluminescent material, the first additive is a group of CuI, Cu, and potassium carbonate.

In the method for manufacturing the electroluminescent material, the step of reacting the third reactant and the first intermediate product to generate the second intermediate product, a relationship between a molar weight of the third reactant and a molar weight of the first intermediate product is that for 7 millimoles-10 millimoles of the third reactant, there are 8 millimoles of the first intermediate product.

In the method for manufacturing the electroluminescent material, the third reactant and the first intermediate product are reacted in a second solvent to generate the second intermediate product, the second solvent comprises one or a group selected from toluene, N, N-dimethylformamide, dimethylacetamide, aniline, ethylbenzene, mesitylene, benzaldehyde, diphenyl ether, xylene, diethylbenzene, and chlorobenzene.

In the method for manufacturing the electroluminescent material, the second solvent comprises a second additive, the second additive comprises one or a group selected from tris (dibenzylideneacetone) dipalladium, tri-tert-butylphosphine tetrafluoroborate, sodium tert-butoxide, potassium carbonate, potassium hydroxide, sodium hydroxide, sodium carbonate, and sodium bicarbonate.

In the method for manufacturing the electroluminescent material, the second solvent is a group of tris (dibenzylideneacetone) dipalladium, tri-tert-butylphosphine tetrafluoroborate, and sodium tert-butoxide.

In the method for manufacturing the electroluminescent material, in the step of reacting the second intermediate product and the fourth reactant to generate the electroluminescent material, a relationship between a molar weight of the second intermediate product and a molar weight of the fourth reactant is that for 5 millimoles of the second intermediate product, there are 3 millimoles-7 millimoles of the fourth reactant.

In the method for manufacturing the electroluminescent material, the second intermediate product and the fourth reactant are reacted in a third solvent to generate the electroluminescent material, the third solvent comprises one or a group selected from dichloromethane, chloroform, acetone, toluene, aniline, ethylbenzene, mesitylene, benzaldehyde, diphenyl ether, xylene, diethylbenzene, and chlorobenzene.

In the method for manufacturing the electroluminescent material, the third solvent comprises a third additive, the third additive comprises one or a group selected from sodium hydroxide, tri-tert-butylphosphine tetrafluoroborate, sodium tert-butoxide, potassium carbonate, potassium hydroxide, sodium carbonate, and sodium bicarbonate.

In the method for manufacturing the electroluminescent material, the third solvent is sodium hydroxide.

In the method for manufacturing the electroluminescent material, the fourth reactant comprises one or a group selected from m-chloroperoxybenzoic acid, peroxybenzoic acid, m-phenylperoxybenzoic acid, tert-butyl peroxybenzoate, and hydrogen peroxide.

The present disclosure provides a luminescent device, comprising:

a substrate base layer, wherein the substrate layer comprises a base and an anode layer, and the anode layer is formed on the base;

a hole injection layer, wherein the hole injection layer is formed on the anode layer;

a hole transport layer, wherein the hole transport layer is formed on the hole injection layer;

a luminescent layer, wherein the luminescent layer is formed on the hole transport layer;

an electronic transport layer, wherein the electronic transport layer is formed on the luminescent layer; and a cathode layer, wherein the cathode layer is formed on the electronic transport layer;

wherein the luminescent layer comprises an electroluminescent material, wherein a structural formula of the electroluminescent material is $R_3$—$R_1$—$R_2$, wherein a structural formula of the $R_1$ group is selected from one of

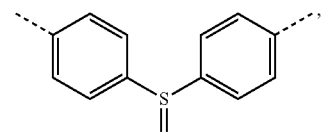

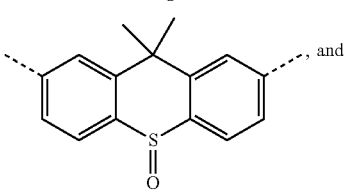

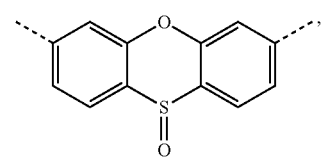

a structural formula of the R2 group is selected from one of

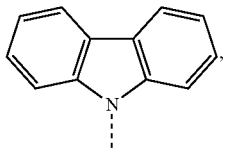

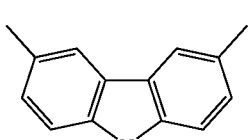

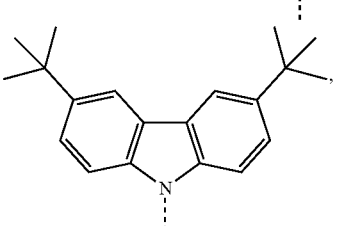

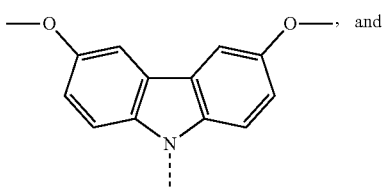

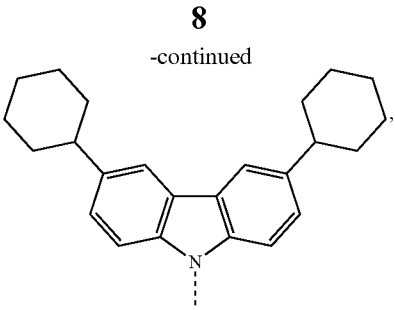

a structural formula of the $R_3$ group is selected from one of

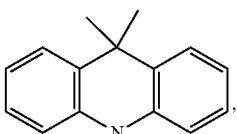

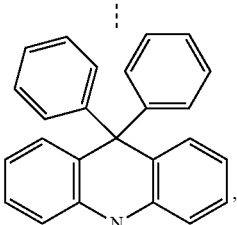

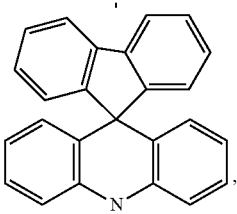

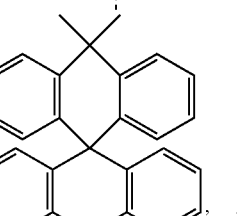

, and

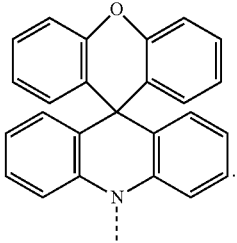

The benefit is the present disclosure provides an electroluminescent material, a method for manufacturing the electroluminescent material, and a luminescent device, by reacting a first reactant and a second reactant to generate a first intermediate product, reacting the first intermediate product and a third reactant to generate a second intermediate product, and reacting the second intermediate product and a fourth reactant to generate the electroluminescent material, by employing different electron donor units and electron acceptor units of acridine and carbazoles, and using two different donors to connect to an acceptor to form an asymmetric structure, acridine electron donor units are responsible for controlling the lowest single triplet energy level of a target molecule, and carbazoles acceptor units are responsible for adjusting the spectrum, an electroluminescent material, a method for manufacturing the electroluminescent material, and a luminescent device capable of emitting dark blue light with a high luminous efficiency are achieved.

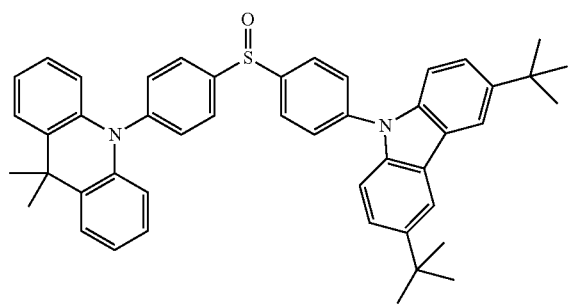 [SMILES: CC(C)(C)c1ccc2c(c1)c1cc(C(C)(C)C)ccc1n2-c1ccc(S(=O)c2ccc(N3c4ccccc4C(C)(C)c4ccccc43)cc2)cc1]

and an electroluminescent material

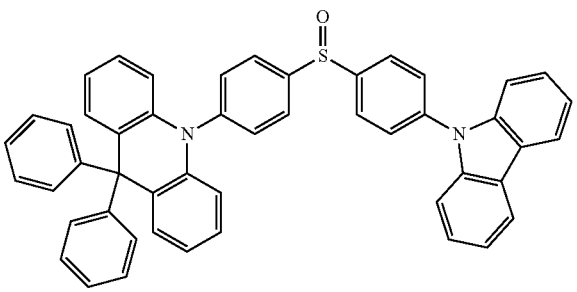 [SMILES: O=S(c1ccc(N2c3ccccc3C(c3ccccc3)(c3ccccc3)c3ccccc32)cc1)c1ccc(-n2c3ccccc3c3ccccc32)cc1]

in a toluene solution of the present application.

Figure 2:
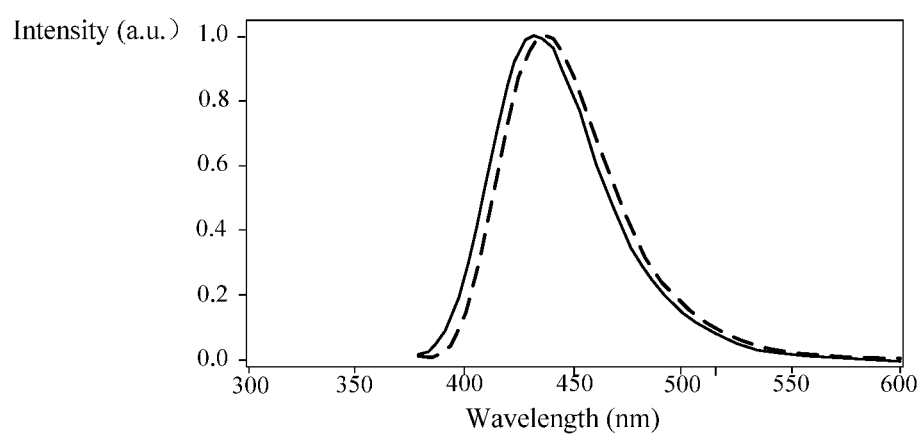
Figure 2:
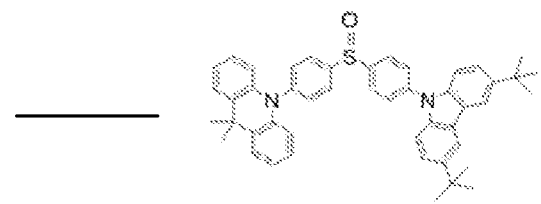
Figure 2:
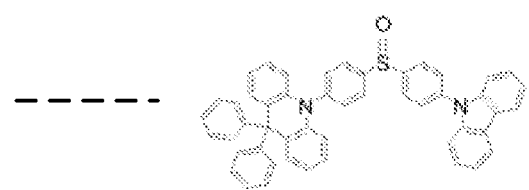

FIG. 2 is a fluorescence spectrogram of an electroluminescent material

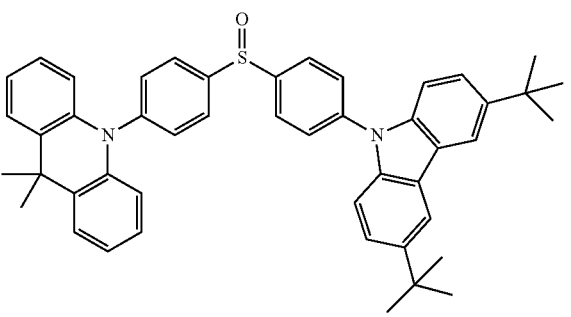 [SMILES: CC(C)(C)c1ccc2c(c1)c1cc(C(C)(C)C)ccc1n2-c1ccc(S(=O)c2ccc(N3c4ccccc4C(C)(C)c4ccccc43)cc2)cc1]

and an electroluminescent material

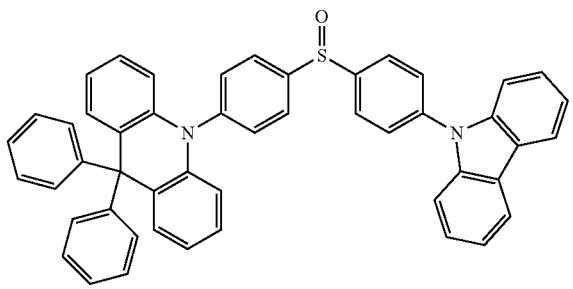 [SMILES: O=S(c1ccc(N2c3ccccc3C(c3ccccc3)(c3ccccc3)c3ccccc32)cc1)c1ccc(-n2c3ccccc3c3ccccc32)cc1]

in a toluene solution of the present application.

Figure 3:
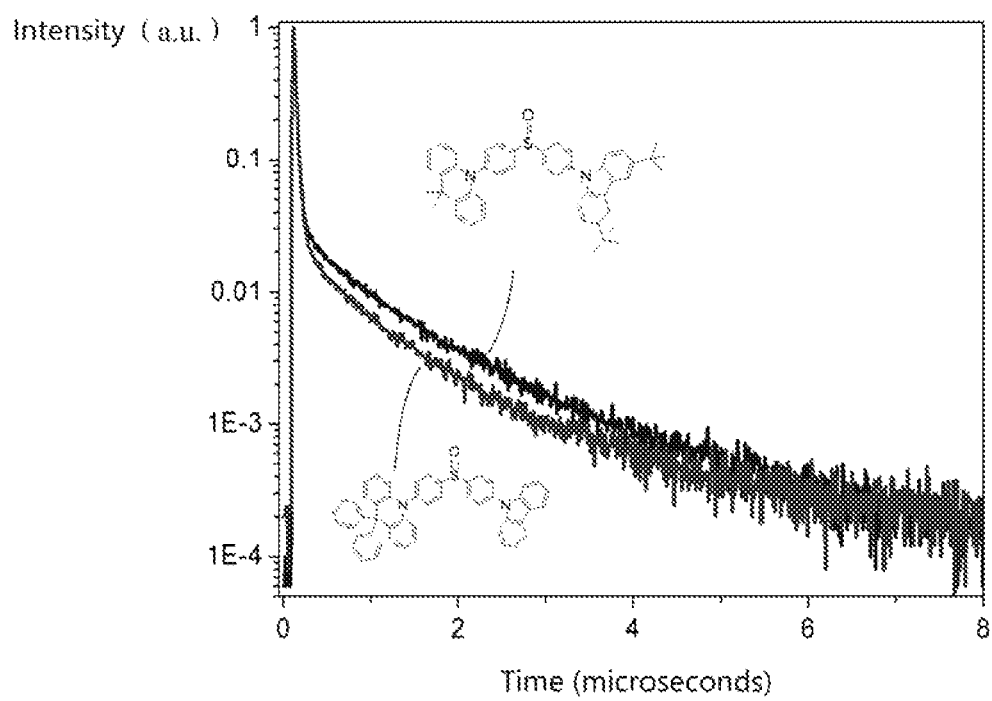

FIG. 3 is a transient fluorescence emission spectrogram of an electroluminescent material

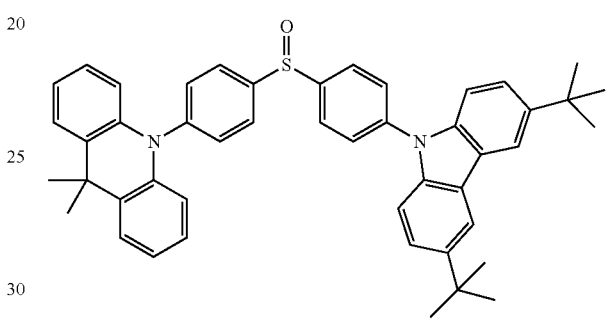

and an electroluminescent material

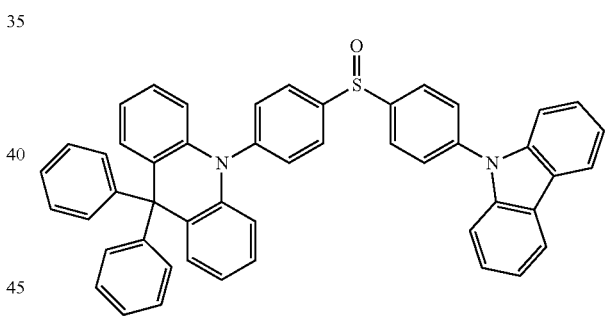

in a toluene solution of the present application.

Figure 4:
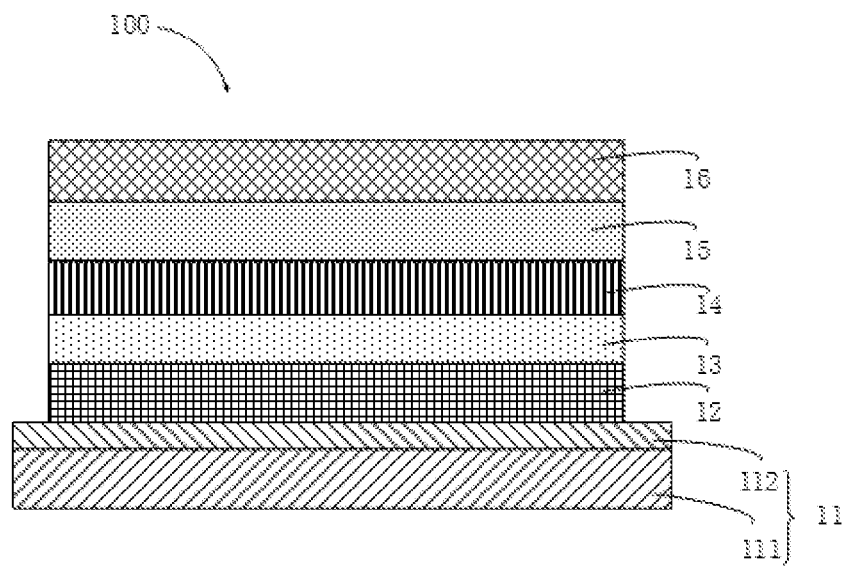

FIG. 4 is a structural diagram of a luminescent device of the present application.

DETAILED DESCRIPTION OF PREFERRED EMBODIMENTS

The present disclosure provides an electroluminescent material. A structural formula of the electroluminescent material is $R_3—R_1—R_2$. A structural formula of the $R_1$ group is selected from one of

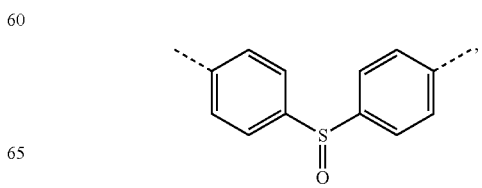

-continued

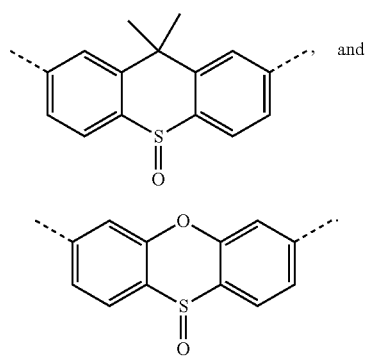
and

A structural formula of the R₂ group is selected from one of

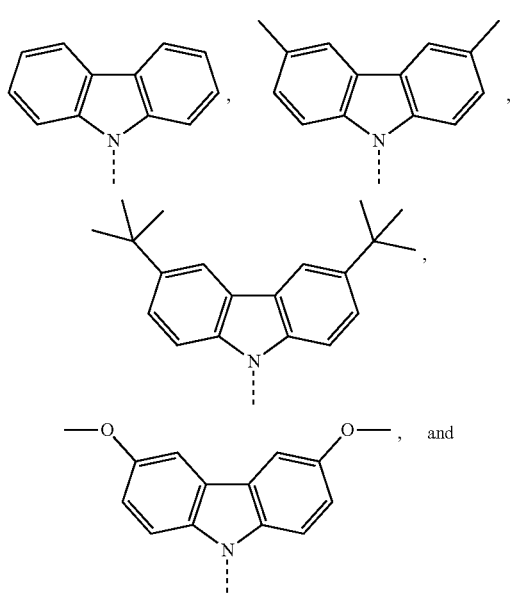
, and

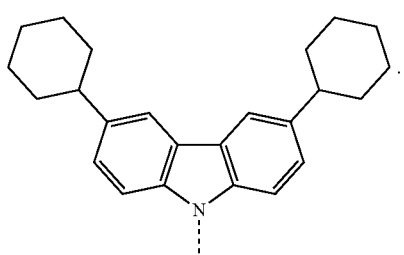

A structural formula of the R₃ group is selected from one of

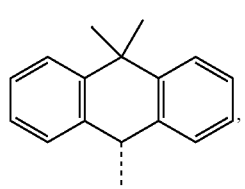
,

-continued

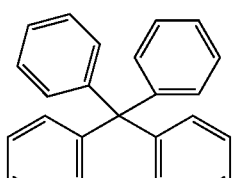
,

[additional structures shown], and

The electroluminescent material is a thermally activated delayed fluorescence (TADF) material capable of emitting mazarine blue light. Through the combination of the R₁ group, the R₂ group, and the R₃ group, the electroluminescent material has 75 different structural formulas. The electroluminescent material has an asymmetric structure. In a few of embodiment, formulas of the electroluminescent materials includes

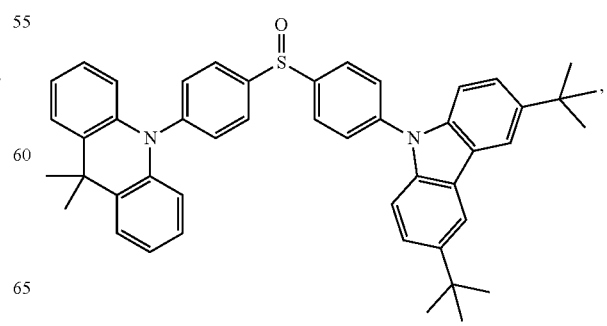

-continued

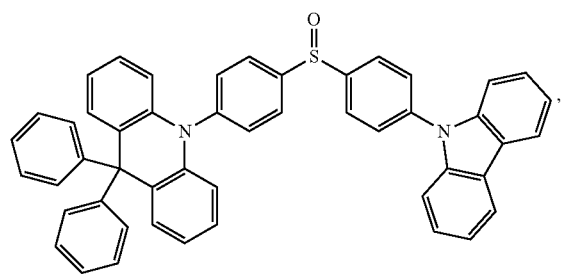

and so on.

The present disclosure further provides a method for manufacturing the electroluminescent material including:

A, providing a first reactant and a second reactant, and reacting the first reactant and the second reactant to generate a first intermediate product, wherein a structural formula of the first reactant is $X_1$—$R_4$—$X_2$, wherein a structural formula of the $R_4$ group is selected from one of

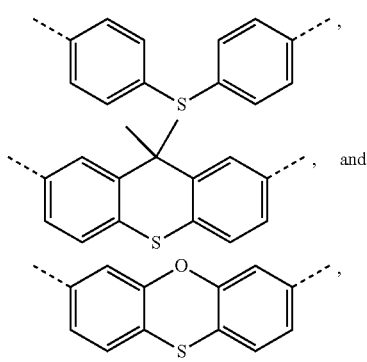

and

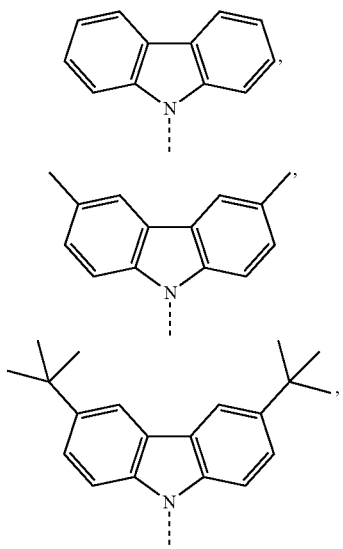

the $X_1$ group is Cl or Br, the $X_2$ group is Br or I, the $X_1$ group is different from the $X_2$ group, the second reactant includes a compound containing a $R_2$ group, a structural formula of the $R_2$ group is selected from one of

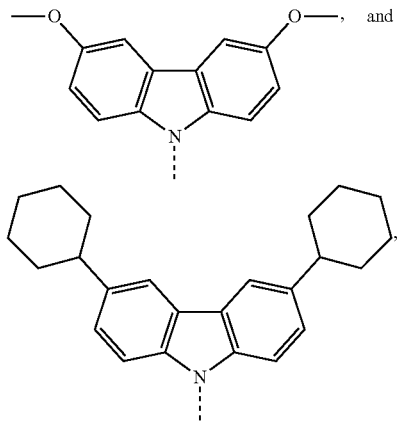

a structural formula of the first intermediate product is $X_1$—$R_4$—$R_2$.

A structural formula of the first reactant can be one of Br—$R_4$—I, Cl—$R_4$—I, and Cl—$R_4$—Br. A structural formula of the second reactant can be H—$R_2$.

A reaction formula of reacting the first reactant and the second reactant to generate a first intermediate product is:

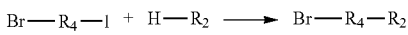

In one embodiment, in the step of reacting the first reactant and the second reactant to generate a first intermediate product, a relationship between a molar weight of the first reactant and a molar weight of the second reactant is that for 10 millimoles of the first reactant, there are 5 millimoles-15 millimoles of the second reactant. Specifically, the relationship between a molar weight of the first reactant and a molar weight of the second reactant can be that for 10 millimoles of the first reactant, there are 11 millimoles of the second reactant, or the relationship between a molar weight of the first reactant and a molar weight of the second reactant can be that for 1 mole of the first reactant, there is 1 mole of the second reactant.

In one embodiment, the first reactant and the second reactant are reacted in a first solvent to generate the first intermediate product, the first solvent includes one or a group selected from N, N-dimethylformamide, dimethylacetamide, toluene, aniline, ethylbenzene, mesitylene, benzaldehyde, diphenyl ether, xylene, diethylbenzene, and chlorobenzene.

In one embodiment, the first solvent includes a first additive, the first additive includes one or a group selected from CuI, Cu, potassium carbonate, tri-tert-butylphosphine tetrafluoroborate, sodium tert-butoxide, potassium hydroxide, sodium hydroxide, sodium carbonate and sodium bicarbonate.

In one embodiment, the structural formula of the first reactant can be

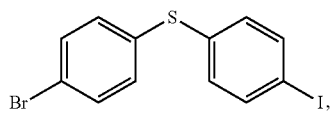 [SMILES: Brc1ccc(Sc2ccc(I)cc2)cc1]

the structural formula of the second reactant can be

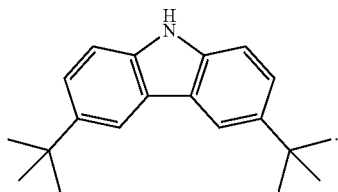 [SMILES: CC(C)(C)c1ccc2[nH]c3ccc(C(C)(C)C)cc3c2c1]

In one embodiment, a reaction formula of reacting the first reactant and the second reactant to generate the first intermediate is:

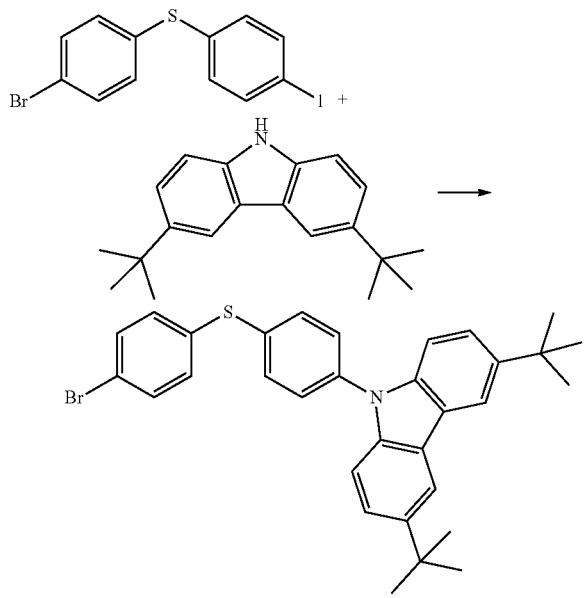

In one embodiment, 10 millimoles of the first reactant

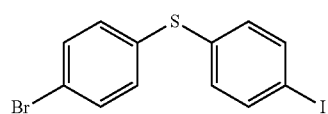 [SMILES: Brc1ccc(Sc2ccc(I)cc2)cc1]

and 11 millimoles of the second reactant

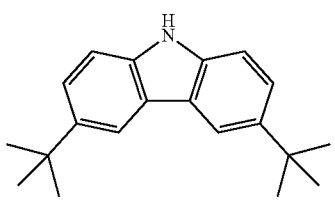 [SMILES: CC(C)(C)c1ccc2[nH]c3ccc(C(C)(C)C)cc3c2c1]

are added to a 100 ml schrank bottle, and CuI, Cu, and potassium carbonate are added, passing argon for ventilation, N, N-dimethylformamide are added, and those are reacted under the protection of argon for 24 hours to obtain a first mixture including the first intermediate product, a separated and purified process is employed to the first mixture to obtain the first intermediate product

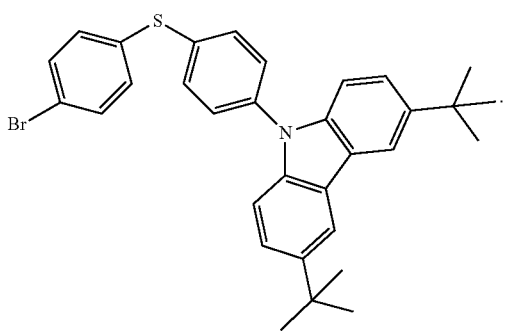 [SMILES: CC(C)(C)c1ccc2c(c1)c1cc(C(C)(C)C)ccc1n2-c1ccc(Sc2ccc(Br)cc2)cc1]

In a few of embodiment, the first intermediate product is a white solid, and a yield of the first intermediate product was 84%.

In one embodiment, the structural formula of the first reactant can be

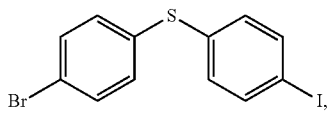 [SMILES: Brc1ccc(Sc2ccc(I)cc2)cc1]

the structural formula of the second reactant can be

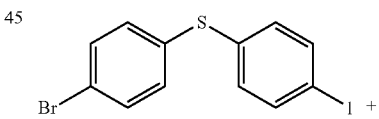

In one embodiment, a reaction formula of reacting the first reactant and the second reactant to generate the first intermediate is:

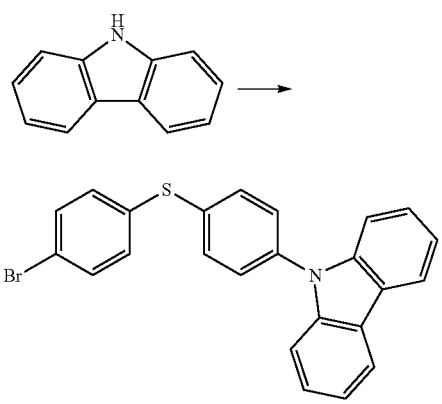

In one embodiment, 10 millimoles of the first reactant

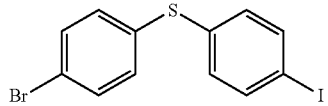 [SMILES: Brc1ccc(Sc2ccc(I)cc2)cc1]

and 11 millimoles of the second reactant

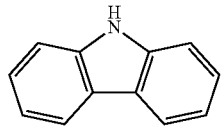 [SMILES: c1ccc2c(c1)[nH]c1ccccc12]

are added to a 100 ml schrank bottle, and CuI, Cu, and potassium carbonate are added, passing argon for ventilation, N, N-dimethylformamide are added, and those are reacted under the protection of argon for 24 hours to obtain a first mixture including the first intermediate product, a separated and purified process is employed to the first mixture to obtain the first intermediate product

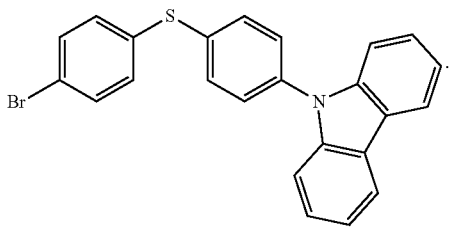 [SMILES: Brc1ccc(Sc2ccc(-n3c4ccccc4c4ccccc43)cc2)cc1]

In a few of embodiment, the first intermediate product is a white solid, and a yield of the first intermediate product was 86%.

B, providing a third reactant, and reacting the third reactant and the first intermediate product to generate a second intermediate product, wherein the third reactant includes a compound containing a $R_3$ group, a structural formula of the $R_3$ group is selected from one of

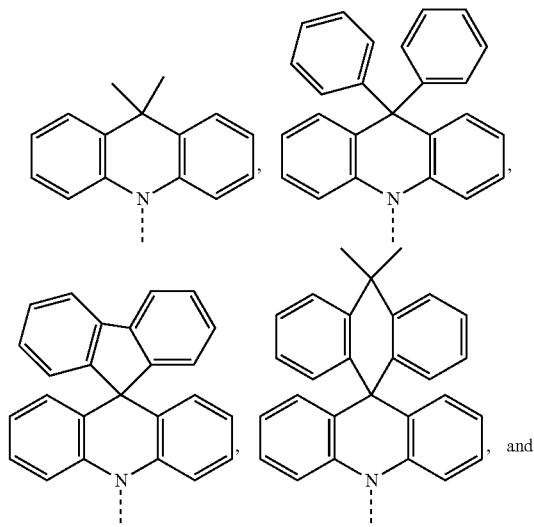, and

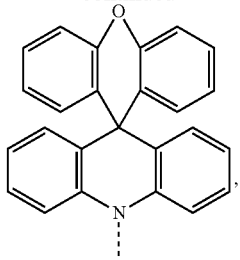

a structural formula of the second intermediate product is $R_3$—$R_4$—$R_2$.

A structural formula of the third reactant can be H—$R_3$.

A reaction formula of reacting the third reactant and the first intermediate product to generate a second intermediate product is:

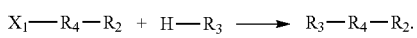

In one embodiment, in the step of reacting the third reactant and the first intermediate product to generate the second intermediate product, a relationship between a molar weight of the third reactant and a molar weight of the first intermediate product is that for 7 millimoles-10 millimoles of the third reactant, there are 8 millimoles of the first intermediate product. Specifically, a relationship between a molar weight of the third reactant and a molar weight of the first intermediate product is that for 8.8 millimoles of the third reactant, there are 8 millimoles of the first intermediate product, or a relationship between a molar weight of the third reactant and a molar weight of the first intermediate product is that for 1 mole of the third reactant, there is 1 mole of the first intermediate product.

In one embodiment, the third reactant and the first intermediate product are reacted in a second solvent to generate the second intermediate product, the second solvent includes one or a group selected from toluene, N, N-dimethylformamide, dimethylacetamide, aniline, ethylbenzene, mesitylene, benzaldehyde, diphenyl ether, xylene, diethylbenzene, and chlorobenzene.

In one embodiment, the second solvent includes a second additive, the second additive includes one or a group selected from tris (dibenzylideneacetone) dipalladium, tri-tert-butylphosphine tetrafluoroborate, sodium tert-butoxide, potassium carbonate, potassium hydroxide, sodium hydroxide, sodium carbonate, and sodium bicarbonate.

In one embodiment, the structural formula of the third reactant can be

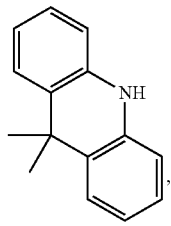 [SMILES: CC1(C)c2ccccc2Nc2ccccc21]

the structural formula of the first intermediate product can be

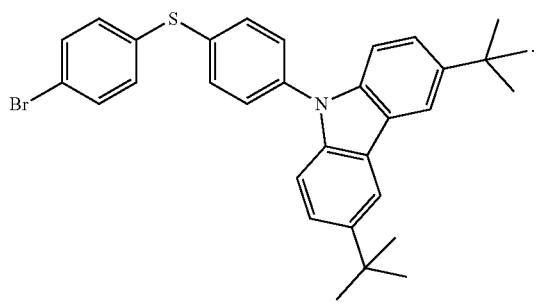 [SMILES: CC(C)(C)c1ccc2c(c1)c1cc(C(C)(C)C)ccc1n2-c1ccc(Sc2ccc(Br)cc2)cc1]

In one embodiment, a reaction formula of reacting the third reactant and the first intermediate product to generate the second intermediate product is:

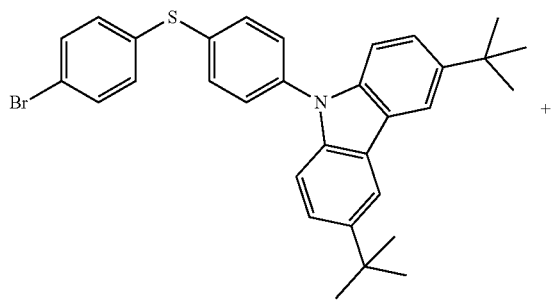

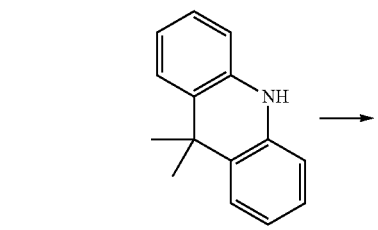

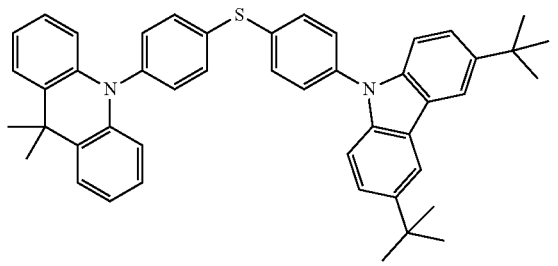

In one embodiment, 8.8 millimoles of the third reactant

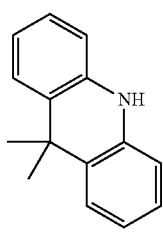 [SMILES: CC1(C)c2ccccc2Nc2ccccc21]

and 8 millimoles of the first intermediate product

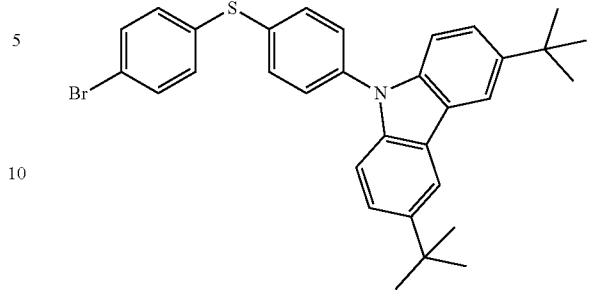

are added to a 100 ml schrank bottle, and tris (dibenzylideneacetone) dipalladium, tri-tert-butylphosphine tetrafluoroborate, and sodium tert-butoxide are added, passing argon for ventilation, toluene are added, and those are reacted under the protection of argon for 24 hours to obtain a second mixture including the second intermediate product, a separated and purified process is employed to the second mixture to obtain the second intermediate product

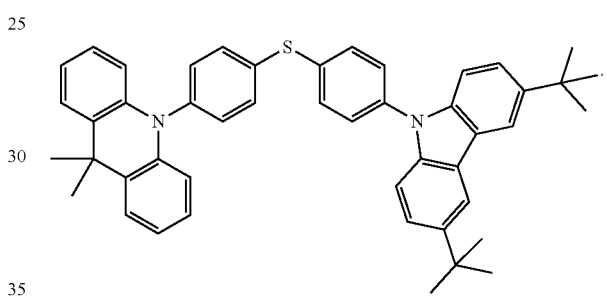

In a few of embodiment, the second intermediate product is a white solid, and a yield of the second intermediate product was 85%.

In one embodiment, the structural formula of the third reactant can be

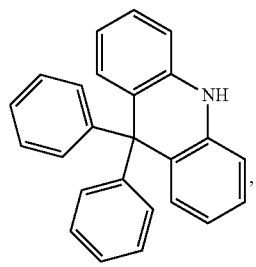 [SMILES: c1ccc(C2(c3ccccc3)c3ccccc3Nc3ccccc32)cc1]

the structural formula of the first intermediate product can be

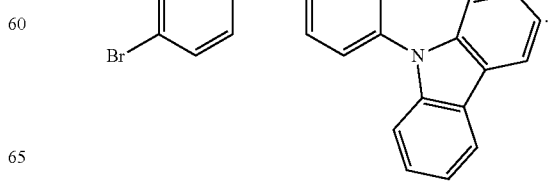

In one embodiment, a reaction formula of reacting the third reactant and the first intermediate product to generate the second intermediate product is:

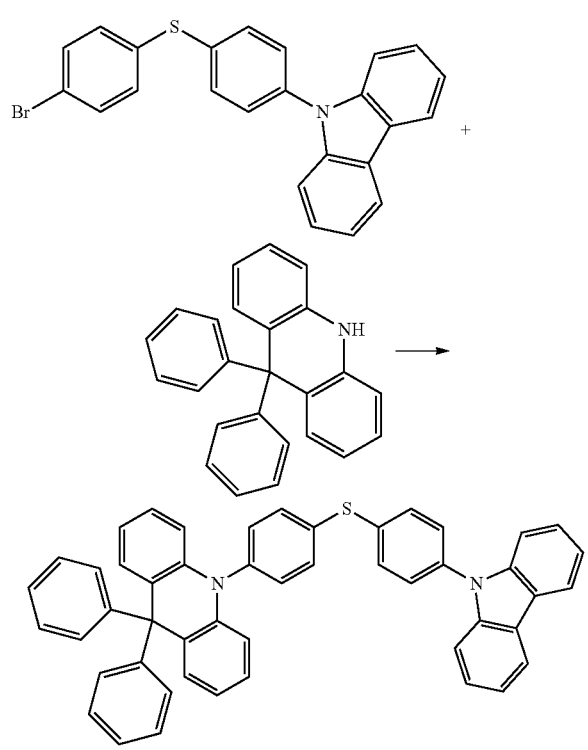

In one embodiment, 8.8 millimoles of the third reactant

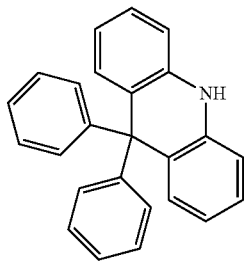 [SMILES: c1ccc(C2(c3ccccc3)c3ccccc3Nc3ccccc32)cc1]

and 8 millimoles of the first intermediate product

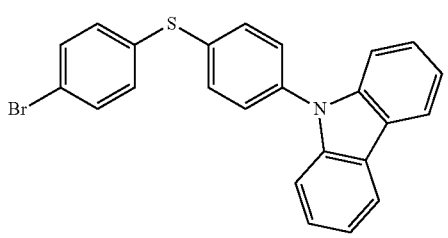 [SMILES: Brc1ccc(Sc2ccc(-n3c4ccccc4c4ccccc43)cc2)cc1]

are added to a 100 ml schrank bottle, and tris (dibenzylideneacetone) dipalladium, tri-tert-butylphosphine tetrafluoroborate, and sodium tert-butoxide are added, passing argon for ventilation, toluene are added, and those are reacted under the protection of argon for 24 hours to obtain a second mixture including the second intermediate product, a separated and purified process is employed to the second mixture to obtain the second intermediate product

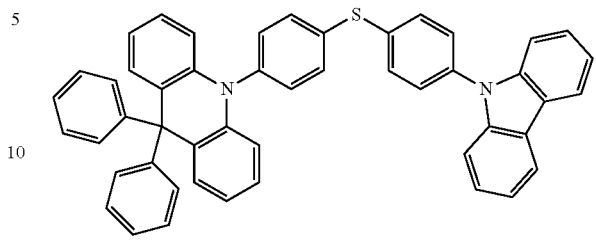

In a few of embodiment, the second intermediate product is a white solid, and a yield of the second intermediate product was 82%.

C, providing a fourth reactant, and reacting the second intermediate product and the fourth reactant to generate the electroluminescent material, wherein the fourth reactant is an oxidizing agent, a structural formula of the electroluminescent material is $R_3$—$R_1$—$R_2$, a structural formula of the $R_1$ group is selected from one of

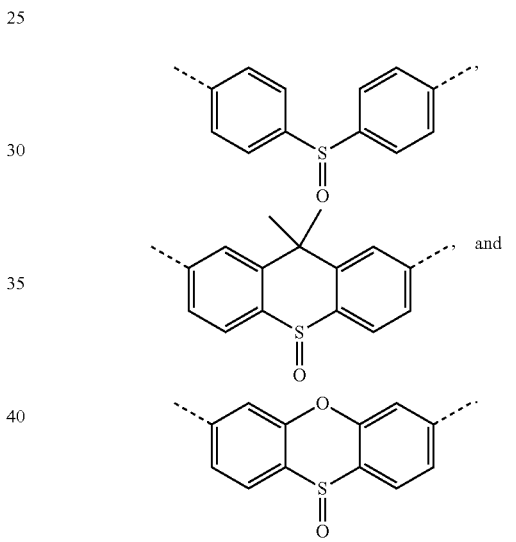

The fourth reactant includes one or a group selected from m-chloroperoxybenzoic acid, peroxybenzoic acid, m-phenylperoxybenzoic acid, tert-butyl peroxybenzoate, and hydrogen peroxide.

In one embodiment, in the step of reacting the second intermediate product and the fourth reactant to generate the electroluminescent material, a relationship between a molar weight of the second intermediate product and a molar weight of the fourth reactant is that for 5 millimoles of the second intermediate product, there are 3 millimoles-7 millimoles of the fourth reactant. Specifically, a relationship between a molar weight of the second intermediate product and a molar weight of the fourth reactant can be that for 5 millimoles of the second intermediate product, there are 6 millimoles of the fourth reactant, or a relationship between a molar weight of the second intermediate product and a molar weight of the fourth reactant can be that for 1 mole of the second intermediate product, there is 1 mole of the fourth reactant.

In one embodiment, the second intermediate product and the fourth reactant are reacted in a third solvent to generate the electroluminescent material, the third solvent includes one or a group selected from dichloromethane, chloroform, acetone, toluene, aniline, ethylbenzene, mesitylene, benzaldehyde, diphenyl ether, xylene, diethylbenzene, and chlorobenzene.

In one embodiment, the third solvent includes a third additive, the third additive includes one or a group selected from sodium hydroxide, tri-tert-butylphosphine tetrafluoroborate, sodium tert-butoxide, potassium carbonate, potassium hydroxide, sodium carbonate, and sodium bicarbonate.

In one embodiment, a structural formula of the second intermediate product can be

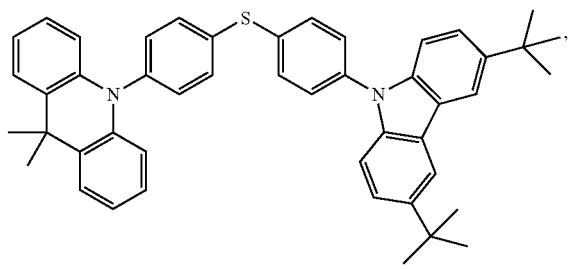 [SMILES: CC(C)(C)c1ccc2c(c1)c1cc(C(C)(C)C)ccc1n2-c1ccc(Sc2ccc(N3c4ccccc4C(C)(C)c4ccccc43)cc2)cc1]

a structural formula of the fourth reactant can be

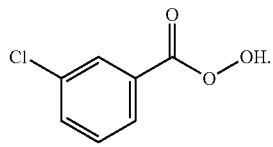 [SMILES: O=C(OO)c1cccc(Cl)c1]

In one embodiment, a reaction formula of reacting the second intermediate product and the fourth reactant to generate the electroluminescent material is:

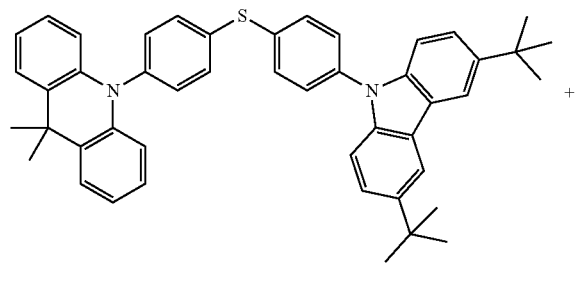

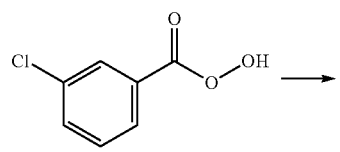

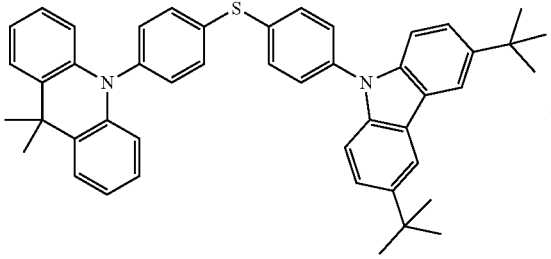

In one embodiment, 40 ml of dichloromethane and 5 millimoles of second intermediate product

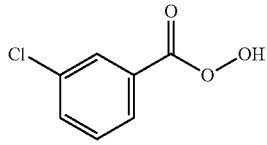 [SMILES: O=C(OO)c1cccc(Cl)c1]

are added to a single mouth bottle, the third reactant

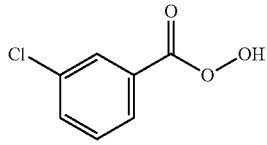 [SMILES: O=C(OO)c1cccc(Cl)c1]

was added in portions of 6.6 millimoles, those are stirred and reacted at 0° C. for 2 hours, sodium hydroxide was added, and those are stirred and reacted continually for 0.5 hours to obtain a third mixture including the electroluminescent material, a separated and purified process is employed to the third mixture to obtain the electroluminescence material

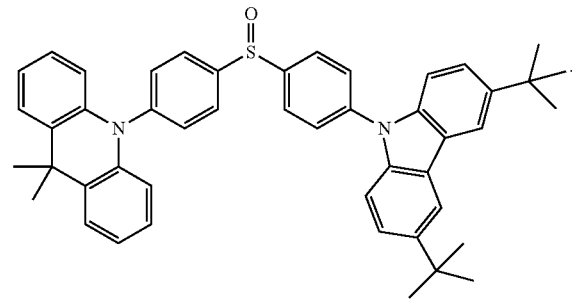 [SMILES: CC(C)(C)c1ccc2c(c1)c1cc(C(C)(C)C)ccc1n2-c1ccc(S(=O)c2ccc(N3c4ccccc4C(C)(C)c4ccccc43)cc2)cc1]

In a few of embodiment, the electroluminescence material is a white solid, and a yield of the electroluminescence material was 81%.

In one embodiment, a structural formula of the second intermediate product can be

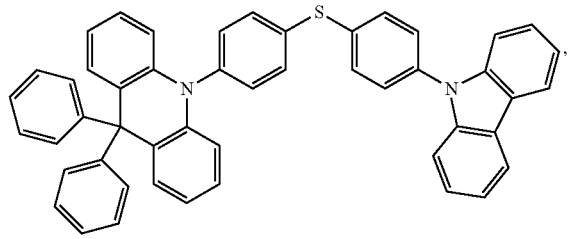 [SMILES: c1ccc(C2(c3ccccc3)c3ccccc3N(c3ccc(Sc4ccc(-n5c6ccccc6c6ccccc65)cc4)cc3)c3ccccc32)cc1]

a structural formula of the fourth reactant can be

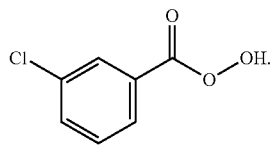 [SMILES: O=C(OO)c1cccc(Cl)c1]

In one embodiment, a reaction formula of reacting the second intermediate product and the fourth reactant to generate the electroluminescent material is:

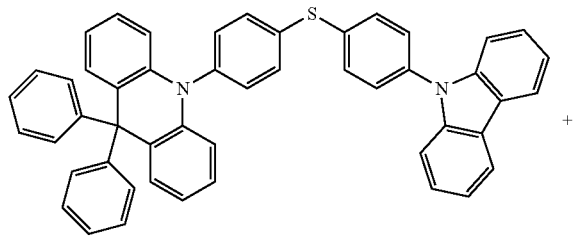

In one embodiment, 40 ml of dichloromethane and 5 millimoles of second intermediate product

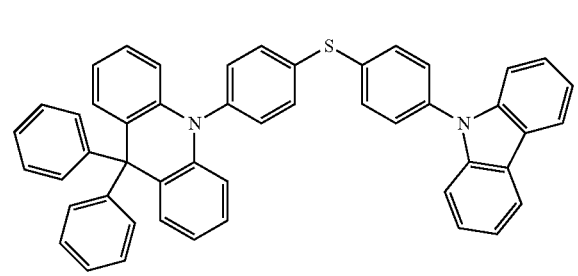 [SMILES: c1ccc(C2(c3ccccc3)c3ccccc3N(c3ccc(Sc4ccc(-n5c6ccccc6c6ccccc65)cc4)cc3)c3ccccc32)cc1]

are added to a single mouth bottle, the third reactant

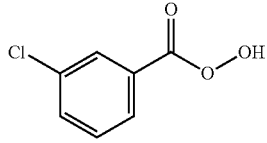 [SMILES: O=C(OO)c1cccc(Cl)c1]

was added in portions of 6.6 millimoles, those are stirred and reacted at 0° C. for 2 hours, sodium hydroxide was added, and those are stirred and reacted continually for 0.5 hours to obtain a third mixture including the electroluminescent material, a separated and purified process is employed to the third mixture to obtain the electroluminescence material

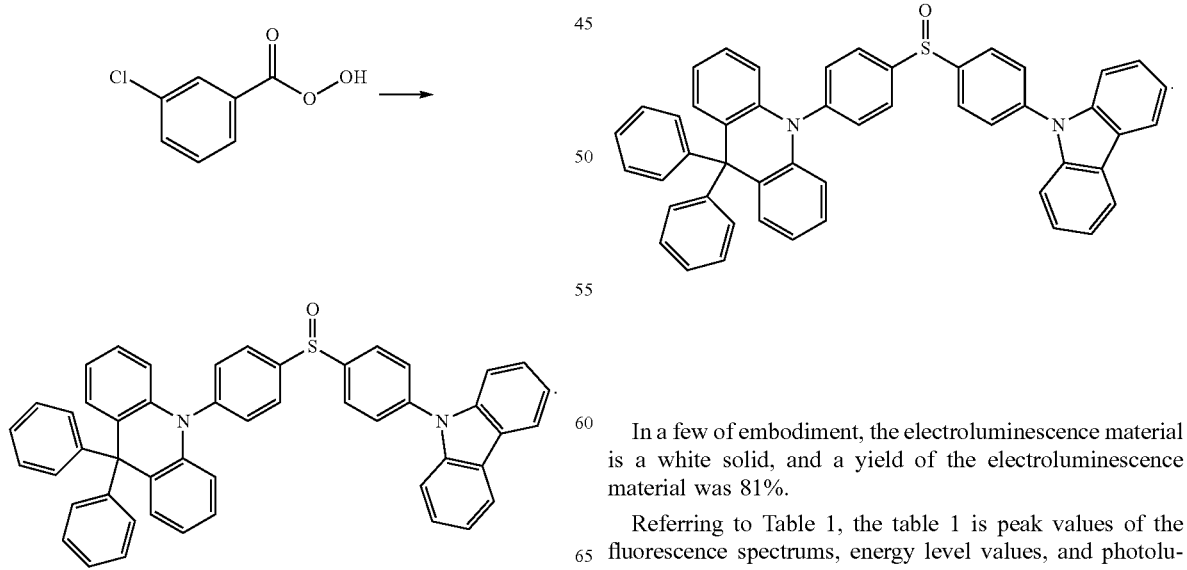

In a few of embodiment, the electroluminescence material is a white solid, and a yield of the electroluminescence material was 81%.

Referring to Table 1, the table 1 is peak values of the fluorescence spectrums, energy level values, and photoluminescence quantum yields of the electroluminescent materials.

| electroluminescent material | PL Peak (nm) | $S_1$ (eV) | $T_1$ (eV) | $E_{ST}$ (eV) | PLQY (%) | HOMO (eV) | LUMO (eV) |
|---|---|---|---|---|---|---|---|
| 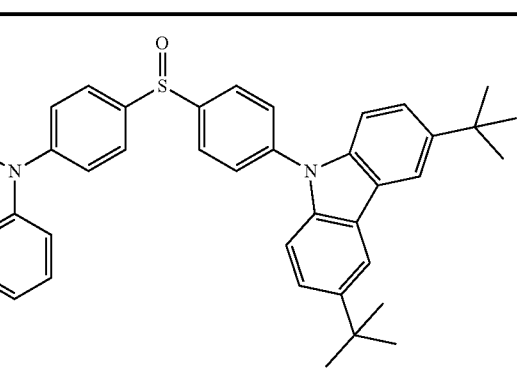 | 433 | 3.16 | 3.10 | 0.06 | 62 | −5.35 | −2.11 |
| 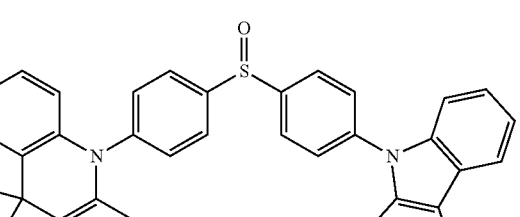 | 437 | 3.12 | 2.97 | 0.05 | 65 | −5.42 | −2.43 |

Wherein, the PL Peak is a peak value of a fluorescence spectrum of the electroluminescent material, $S_1$ is the lowest singlet energy level value, T1 is the lowest triplet energy level value, $\Delta E_{ST}=S_1-T_1$, PLQY is photoluminescence quantum yield, HOMO is the highest occupancy molecular orbital, and LUMO is the lowest unoccupied molecular orbital.

Figure 1:
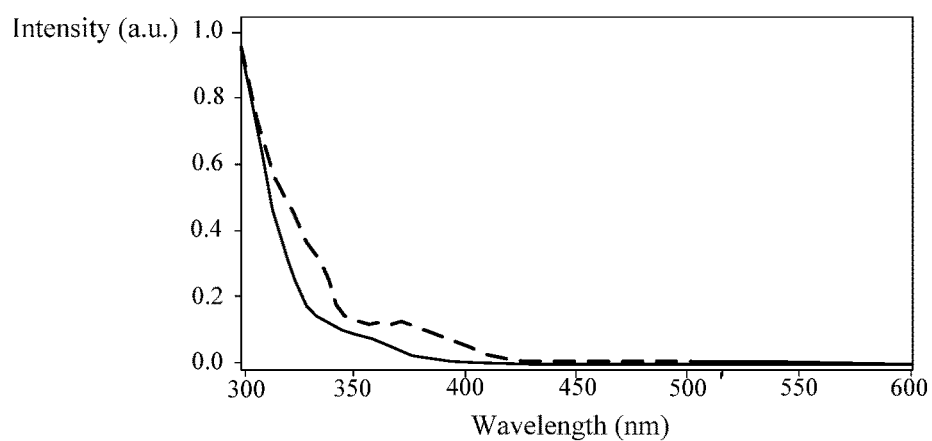
FIG. 1 is an absorption spectrogram of an electroluminescent material
Figure 1:
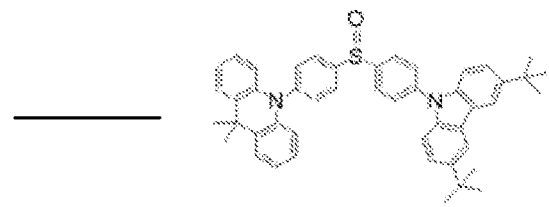
Figure 1:
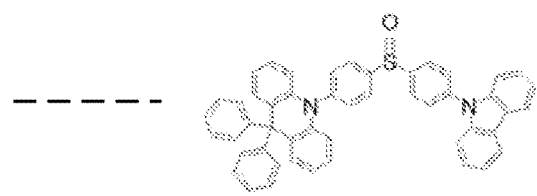

Referring to FIG. 1, FIG. 1 is an absorption spectrogram of an electroluminescent material

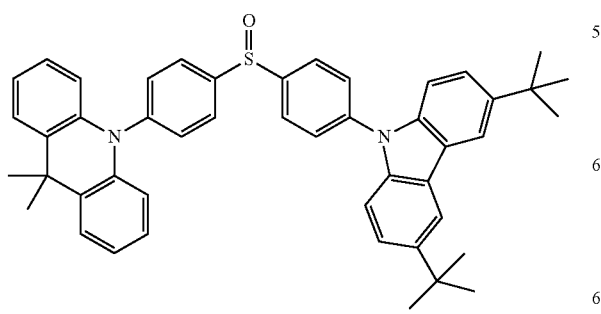

and an electroluminescent material

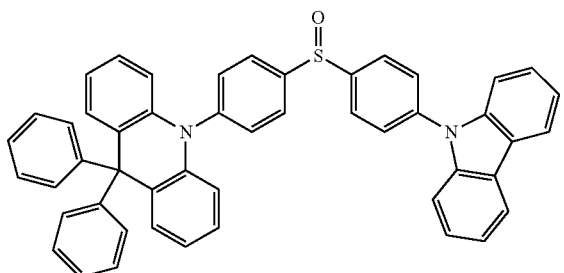

in a toluene solution of the present application. An absorption band of the electroluminescent material provided in the present application is in the ultraviolet region.

Referring to FIG. 2, FIG. 2 is a fluorescence spectrogram of an electroluminescent material

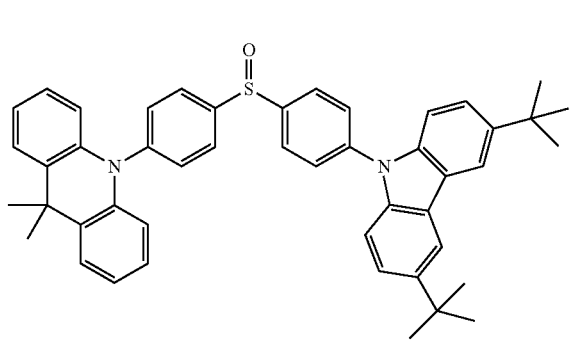 [SMILES: CC(C)(C)c1ccc2c(c1)c1cc(C(C)(C)C)ccc1n2-c1ccc(S(=O)c2ccc(N3c4ccccc4C(C)(C)c4ccccc43)cc2)cc1]

and an electroluminescent material

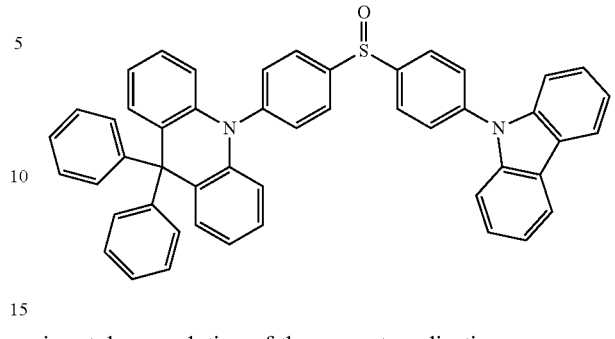

in a toluene solution of the present application. A peak value of a fluorescence emission of the electroluminescent material of the present application is between 425 nm and 450 nm. The wavelength corresponding to the peak value is the wavelength of the blue light. Therefore, the electroluminescent material provided in this application emits blue light when excited.

Referring to FIG. 3, FIG. 3 is a transient fluorescence emission spectrogram of an electroluminescent material

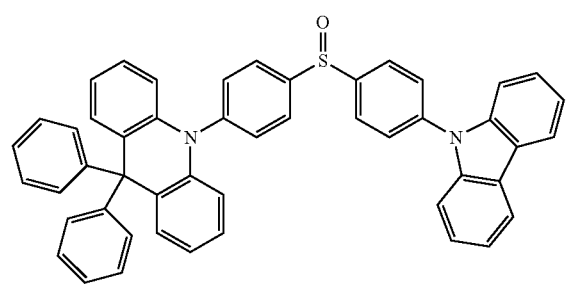 [SMILES: O=S(c1ccc(N2c3ccccc3C(c3ccccc3)(c3ccccc3)c3ccccc32)cc1)c1ccc(-n2c3ccccc3c3ccccc32)cc1]

and an electroluminescent material

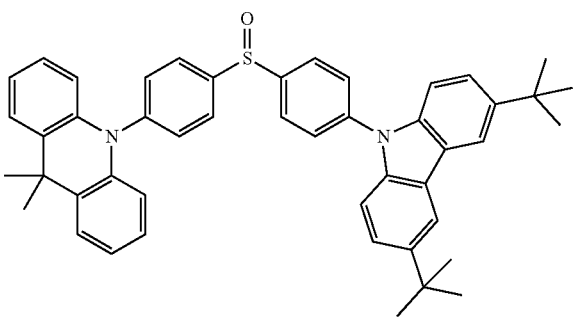 [SMILES: CC(C)(C)c1ccc2c(c1)c1cc(C(C)(C)C)ccc1n2-c1ccc(S(=O)c2ccc(N3c4ccccc4C(C)(C)c4ccccc43)cc2)cc1]

in a toluene solution of the present application.

Referring to FIG. 4, the present application provides a luminescent device 100. The luminescent device includes a substrate layer 11, a hole injection layer 12, a hole transport layer 13, a luminescent layer 14, an electron transport layer 15, and a cathode layer 16.

The substrate layer 11 includes a base 111 and an anode layer 112. The base 111 can be a glass substrate or a transparent plastic substrate. The anode layer 112 is formed on the base 111. The anode layer 112 is made of an indium tin oxide material. The hole injection layer 12 is formed on the anode layer 112. The hole transport layer 13 is formed on the hole injection layer 12. The luminescent layer 14 is formed on the hole transport layer 13. The luminescent layer 14 includes the electroluminescent material, a structural formula of the electroluminescent material is $R_3—R_1—R_2$, wherein a structural formula of the $R_1$ group is selected from one of

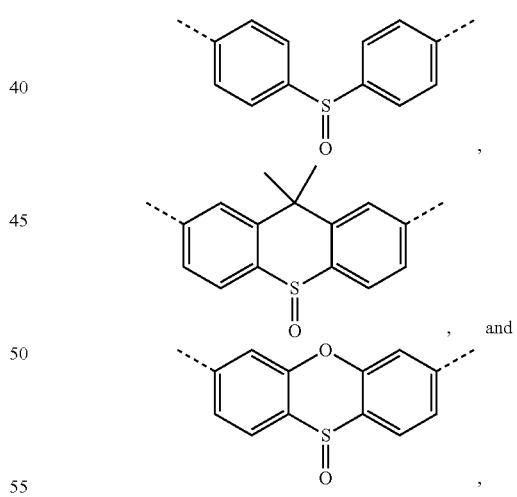

a structural formula of the R2 group is selected from one of

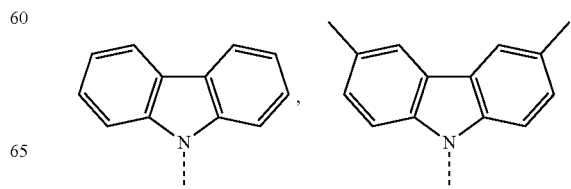

-continued

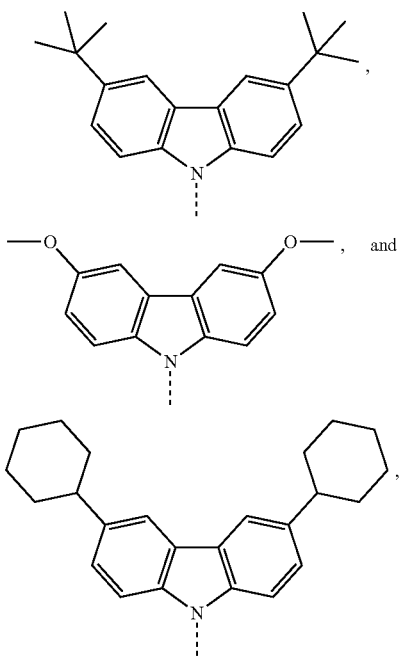

a structural formula of the R₃ group is selected from one of

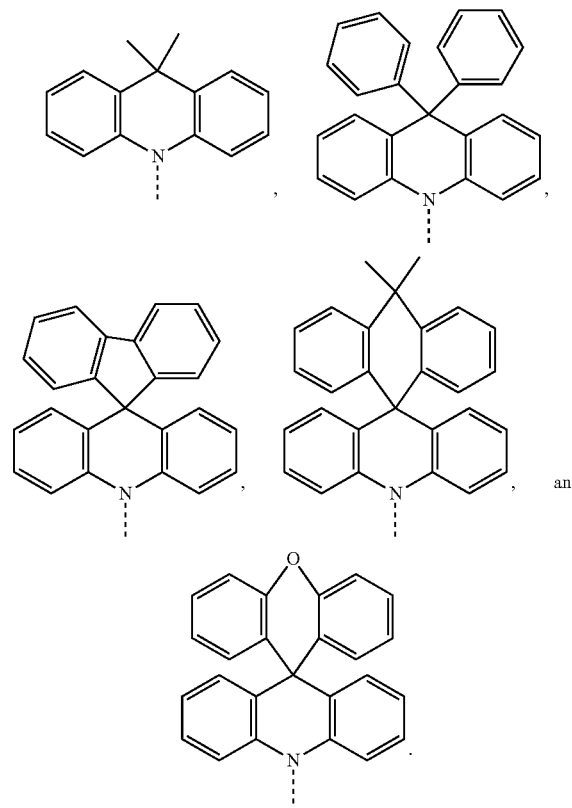

The electron transport layer 15 is formed on the luminescent layer 14. The cathode layer 16 is formed on the electron transport layer 15. The cathode layer 16 can be a lithium fluoride/aluminum material.

The light emitting device 1 and device 2 are manufactured according to a well-known method in the art, the luminescent layer of the device 1 includes

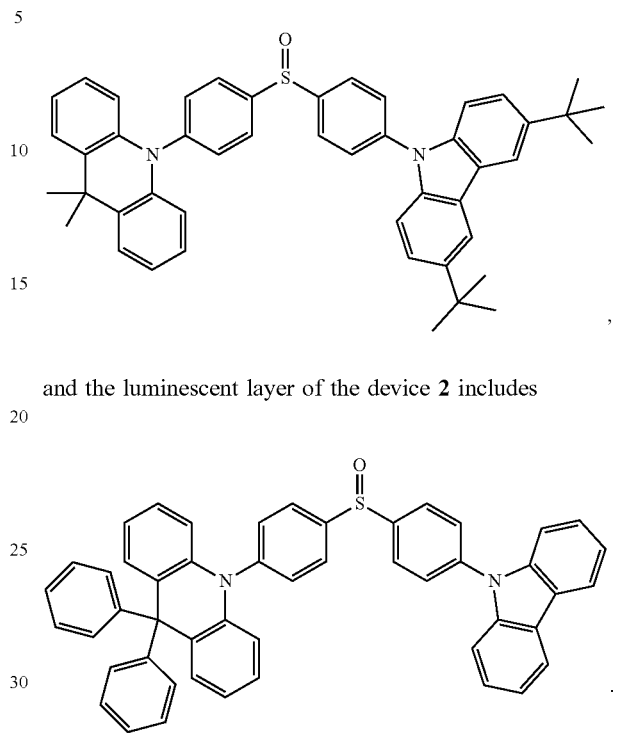

and the luminescent layer of the device 2 includes

Referring to table 2, table 2 is a performance data sheet of the light emitting device of the present application.

TABLE 2

| Device | Maximum Luminance (cd/m²) | FWHM (nm) | EL peak (nm) | Maximum External Quantum Efficiency (%) |
|---|---|---|---|---|
| Device 1 | 1395 | 67 | 689 | 13 |
| Device 2 | 983 | 89 | 735 | 10 |

Wherein, in the Table 2, FWHM is full width at half maxima, and EL peak is electroluminescence peak.

The present disclosure provides an electroluminescent material, a method for manufacturing the electroluminescent material, and a luminescent device, by reacting a first reactant and a second reactant to generate a first intermediate product, reacting the first intermediate product and a third reactant to generate a second intermediate product, and reacting the second intermediate product and a fourth reactant to generate the electroluminescent material, by employing different electron donor units and electron acceptor units of acridine and carbazoles, and using two different donors to connect to an acceptor to form an asymmetric structure, acridine electron donor units are responsible for controlling the lowest single triplet energy level of a target molecule, and carbazoles acceptor units are responsible for adjusting the spectrum, an electroluminescent material, a method for manufacturing the electroluminescent material, and a luminescent device capable of emitting dark blue light with a high luminous efficiency are achieved.

The above provides a detailed description of the embodiments of the present application. Specific examples are used herein to explain the principles and embodiments of the present application. The description of the above embodiments is only used to help understand the application. At the same time, for those skilled in the art, according to the idea of the present application, there will be changes in the specific implementation and the scope of application. In summary, the content of this description should not be understood as a limitation on the present application.

What is claimed is:

1. An electroluminescent material, wherein a structural formula of the electroluminescent material is $R_3$—$R_1$—$R_2$, wherein a structural formula of the $R_1$ group is selected from one of

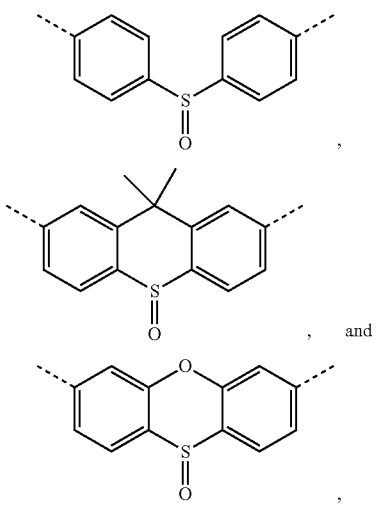

, and a structural formula of the $R_2$ group is selected from one of

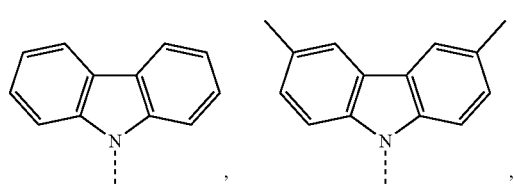

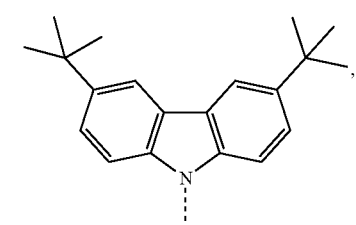

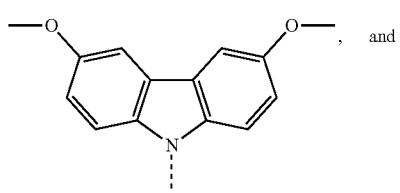

, and a structural formula of the $R_3$ group is selected from one of

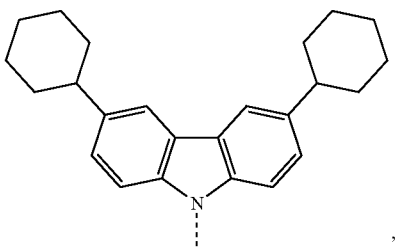

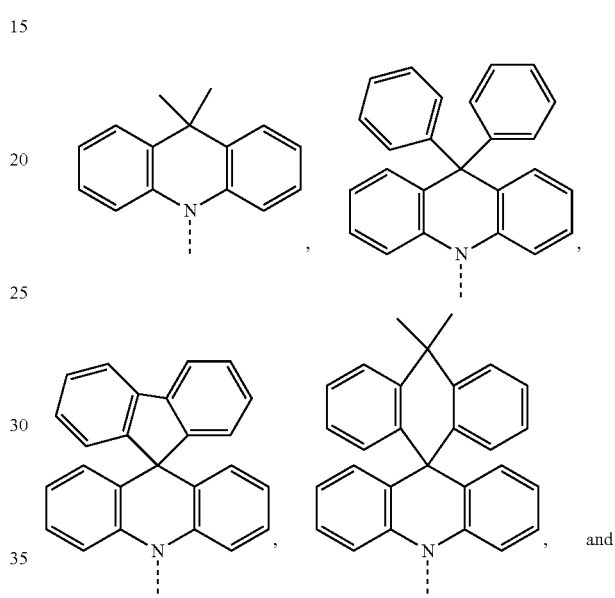

, and

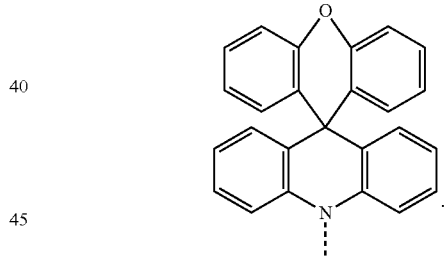

.

2. The electroluminescent material of claim 1, wherein a peak value of a fluorescence emission of the electroluminescent material is between 425 nm and 450 nm.

3. A method for manufacturing an electroluminescent material, comprising:

providing a first reactant and a second reactant, and reacting the first reactant and the second reactant to generate a first intermediate product, wherein a structural formula of the first reactant is $X_1$—$R_4$—$X_2$, wherein a structural formula of the $R_4$ group is selected from one of

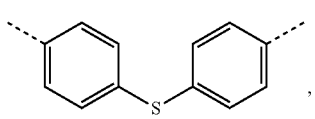

-continued

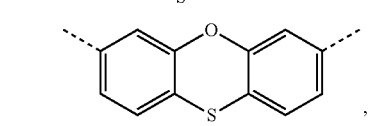, and

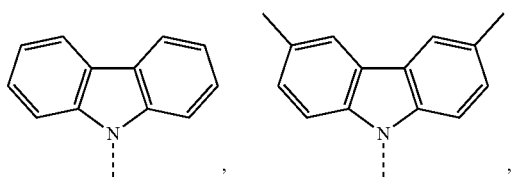, the X₁ group is Cl or Br, the X₂ group is Br or I, the X₁ group is different from the X₂ group, the second reactant comprises a compound containing a R₂ group, a structural formula of the R₂ group is selected from one of

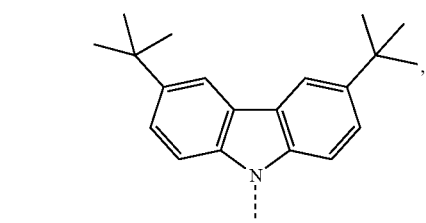,

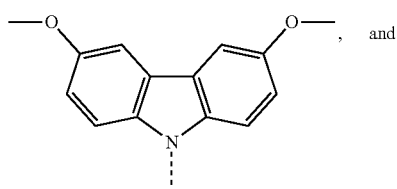,

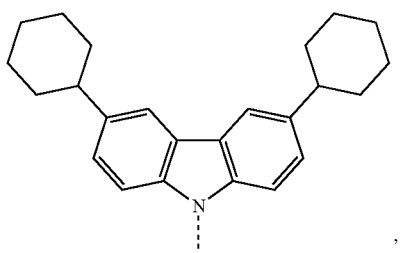,

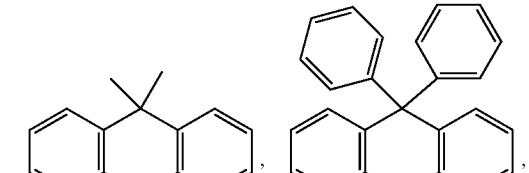,

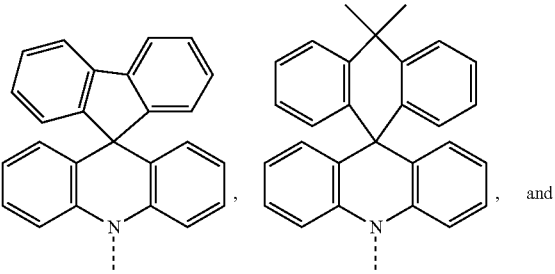, and

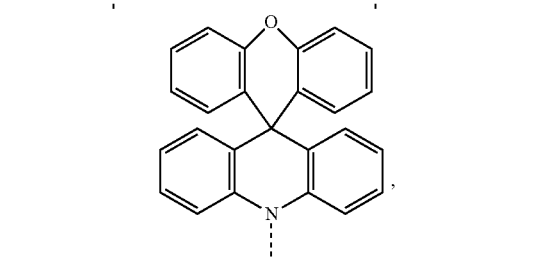, a structural formula of the second intermediate product is R₃R₄R₂; and providing a fourth reactant, and reacting the second intermediate product and the fourth reactant to generate the electroluminescent material, wherein the fourth reactant is an oxidizing agent, a structural formula of the electroluminescent material is R₃—R₁—R₂, a structural formula of the R₁ group is selected from one of

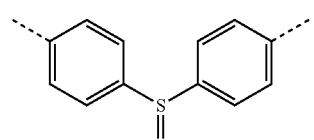,

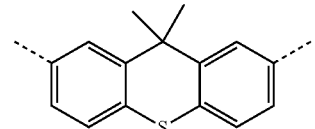, and

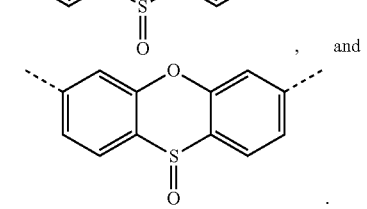.

a structural formula of the first intermediate product is X₁—R₄—X₂;

providing a third reactant, and reacting the third reactant and the first intermediate product to generate a second intermediate product, wherein the third reactant comprises a compound containing a R₃ group, a structural formula of the R₃ group is selected from one of 4. The method for manufacturing the electroluminescent material of claim 3, wherein in the step of reacting the first reactant and the second reactant to generate a first intermediate product, a relationship between a molar weight of the first reactant and a molar weight of the second reactant is that for 10 millimoles of the first reactant, there are 5 millimoles-15 millimoles of the second reactant.

5. The method for manufacturing the electroluminescent material of claim 3, wherein the first reactant and the second reactant are reacted in a first solvent to generate the first intermediate product, the first solvent comprises one or a group selected from N, N-dimethylformamide, dimethylacetamide, toluene, aniline, ethylbenzene, mesitylene, benzaldehyde, diphenyl ether, xylene, diethylbenzene, and chlorobenzene.

6. The method for manufacturing the electroluminescent material of claim 5, wherein the first solvent comprises a first additive, the first additive comprises one or a group selected from CuI, Cu, potassium carbonate, tri-tert-butylphosphine tetrafluoroborate, sodium tert-butoxide, potassium hydroxide, sodium hydroxide, sodium carbonate and sodium bicarbonate.

7. The method for manufacturing the electroluminescent material of claim 6, wherein the first additive is a group of CuI, Cu, and potassium carbonate.

8. The method for manufacturing the electroluminescent material of claim 3, wherein the step of reacting the third reactant and the first intermediate product to generate the second intermediate product, a relationship between a molar weight of the third reactant and a molar weight of the first intermediate product is that for 7 millimoles- 10 millimoles of the third reactant, there are 8 millimoles of the first intermediate product.

9. The method for manufacturing the electroluminescent material of claim 3, wherein the third reactant and the first intermediate product are reacted in a second solvent to generate the second intermediate product, the second solvent comprises one or a group selected from toluene, N, N-dimethylformamide, dimethylacetamide, aniline, ethylbenzene, mesitylene, benzaldehyde, diphenyl ether, xylene, diethylbenzene, and chlorobenzene.

10. The method for manufacturing the electroluminescent material of claim 9, wherein the second solvent comprises a second additive, the second additive comprises one or a group selected from tris (dibenzylideneacetone) dipalladium, tri-tert-butylphosphine tetrafluoroborate, sodium tert-butoxide, potassium carbonate, potassium hydroxide, sodium hydroxide, sodium carbonate, and sodium bicarbonate.

11. The method for manufacturing the electroluminescent material of claim 10, wherein the second solvent is a group of tris (dibenzylideneacetone) dipalladium, tri-tert-butylphosphine tetrafluoroborate, and sodium tert-butoxide.

12. The method for manufacturing the electroluminescent material of claim 3, wherein in the step of reacting the second intermediate product and the fourth reactant to generate the electroluminescent material, a relationship between a molar weight of the second intermediate product and a molar weight of the fourth reactant is that for 5 millimoles of the second intermediate product, there are 3 millimoles-7 millimoles of the fourth reactant.

13. The method for manufacturing the electroluminescent material of claim 3, wherein the second intermediate product and the fourth reactant are reacted in a third solvent to generate the electroluminescent material, the third solvent comprises one or a group selected from dichloromethane, chloroform, acetone, toluene, aniline, ethylbenzene, mesitylene, benzaldehyde, diphenyl ether, xylene, diethylbenzene, and chlorobenzene.

14. The method for manufacturing the electroluminescent material of claim 13, wherein the third solvent comprises a third additive, the third additive comprises one or a group selected from sodium hydroxide, tri-tert-butylphosphine tetrafluoroborate, sodium tert-butoxide, potassium carbonate, potassium hydroxide, sodium carbonate, and sodium bicarbonate.

15. The method for manufacturing the electroluminescent material of claim 14, wherein the third solvent is sodium hydroxide.

16. The method for manufacturing the electroluminescent material of claim 3, wherein the fourth reactant comprises one or a group selected from m-chloroperoxybenzoic acid, peroxybenzoic acid, m-phenylperoxybenzoic acid, tert-butyl peroxybenzoate, and hydrogen peroxide.

17. A luminescent device, comprising:
a substrate base layer, wherein the substrate layer comprises a base and an anode layer, and the anode layer is formed on the base;
a hole injection layer, wherein the hole injection layer is formed on the anode layer;
a hole transport layer, wherein the hole transport layer is formed on the hole injection layer;
a luminescent layer, wherein the luminescent layer is formed on the hole transport layer;
an electronic transport layer, wherein the electronic transport layer is formed on the luminescent layer; and
a cathode layer, wherein the cathode layer is formed on the electronic transport layer;
wherein the luminescent layer comprises an electroluminescent material, wherein a structural formula of the electroluminescent material is $R_3$—$R_1$—$R_2$, wherein a structural formula of the $R_1$ group is selected from one of

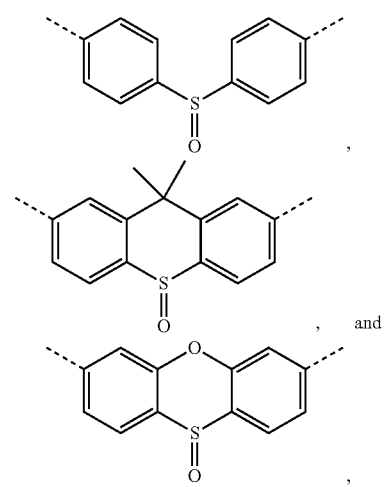

a structural formula of the R2 group is selected from one of

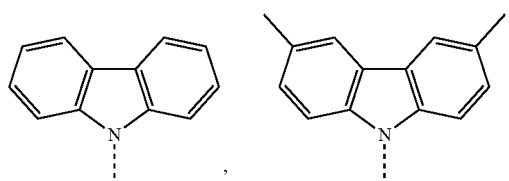

-continued
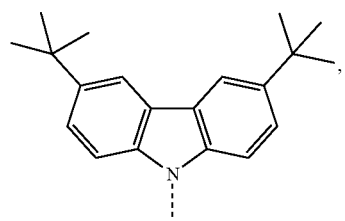
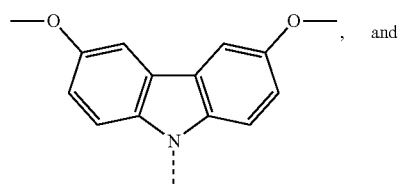 and
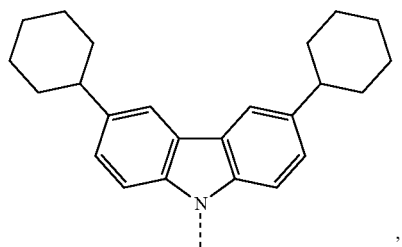
a structural formula of the R₃ group is selected from one of
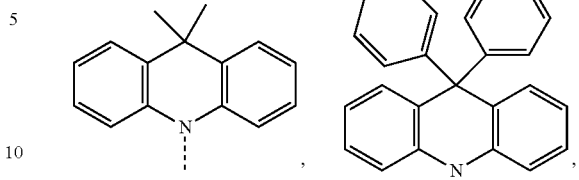
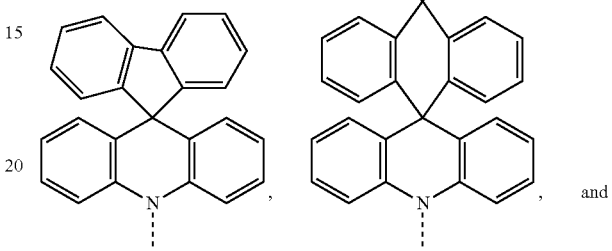 and
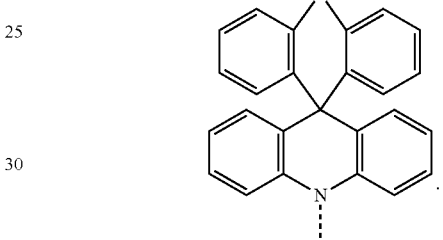
* * * * *